(12) United States Patent
Omi (10) Patent No.: US 9,888,875 B2
(45) Date of Patent: Feb. 13, 2018

(54) DRIVER MONITORING APPARATUS (71) Applicant: DENSO CORPORATION, Kariya, Aichi-pref. (JP)

(72) Inventor: Takuhiro Omi, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

(21) Appl. No.: 15/034,144

(22) PCT Filed: Oct. 9, 2014

(86) PCT No.: PCT/JP2014/005135
§ 371 (c)(1),
(2) Date: May 3, 2016

(87) PCT Pub. No.: WO2015/072069
PCT Pub. Date: May 21, 2015

(65) Prior Publication Data
US 2016/0262682 A1 Sep. 15, 2016

(30) Foreign Application Priority Data

Nov. 13, 2013 (JP) .................................. 2013-235105

(51) Int. Cl.
*G08B 23/00* (2006.01)
*A61B 5/18* (2006.01)
(Continued)

(52) U.S. Cl.
CPC ............. *A61B 5/18* (2013.01); *A61B 5/0077* (2013.01); *A61B 5/1103* (2013.01);
(Continued)

(58) Field of Classification Search
CPC ........... G08B 21/06; A61B 5/18; A61B 5/746; A61B 5/1103; A61B 5/1128; A61B 5/4806; A61B 5/0077; A61B 5/7455; B60K 28/02; B60K 28/06; B60K 28/066; B60W 40/08; B60W 2040/0818
(Continued)

(56) References Cited

U.S. PATENT DOCUMENTS 5,570,698 A * 11/1996 Liang .................... A61B 3/113
340/575
5,867,587 A * 2/1999 Aboutalib .............. G08B 21/06
340/576
(Continued)

FOREIGN PATENT DOCUMENTS

JP   H06-008746      1/1994
JP   H11-185200 A    7/1999
(Continued)

*Primary Examiner* — Thomas Mullen
(74) *Attorney, Agent, or Firm* — Knobbe, Martens, Olson & Bear, LLP (57) ABSTRACT

A driver monitoring system recognizes a state of a driver and determines a recognition stability. When the recognition stability is less than a predetermined reference value, the driver monitoring system makes a request to the driver to perform a different action that is different from an action requested when the recognition stability is not less than the reference value and detects an action of the driver that responds to the request.

7 Claims, 5 Drawing Sheets

(51) Int. Cl.
  *A61B 5/00* (2006.01)
  *A61B 5/11* (2006.01)
  *B60K 28/06* (2006.01)
  *G08B 21/06* (2006.01)

(52) U.S. Cl.
  CPC .......... *A61B 5/1128* (2013.01); *A61B 5/4806* (2013.01); *A61B 5/746* (2013.01); *A61B 5/7455* (2013.01); *B60K 28/06* (2013.01); *G08B 21/06* (2013.01)

(58) Field of Classification Search
  USPC ................. 340/575, 576, 439; 701/1, 70
  See application file for complete search history.

(56) References Cited

U.S. PATENT DOCUMENTS

| | | | | |
|---|---|---|---|---|
| 6,542,081 | B2* | 4/2003 | Torch | A61B 3/0066 340/576 |
| 6,724,920 | B1* | 4/2004 | Berenz | G06K 9/00221 340/575 |
| 6,950,027 | B2* | 9/2005 | Banas | G08B 21/06 340/576 |
| 7,027,621 | B1* | 4/2006 | Prokoski | G06K 9/00255 340/576 |
| 7,719,431 | B2* | 5/2010 | Bolourchi | B60K 28/066 340/439 |
| 2007/0182529 | A1 | 8/2007 | Dobler et al. | |
| 2007/0241914 | A1 | 10/2007 | Ihara et al. | |
| 2008/0204256 | A1 | 8/2008 | Omi | |
| 2008/0231461 | A1* | 9/2008 | Sanchez | G08B 21/06 340/575 |

FOREIGN PATENT DOCUMENTS

| | | |
|---|---|---|
| JP | 2003-296878 A | 10/2003 |
| JP | 2007-219578 A | 8/2007 |
| JP | 2008-137639 A | 6/2008 |
| JP | 2009-31905 A | 2/2009 |
| JP | 2009-48605 A | 3/2009 |
| JP | 2010-20618 A | 1/2010 |
| JP | 2010-187810 A | 9/2010 |
| JP | 2012-11810 A | 1/2012 |
| JP | 2013-41524 A | 2/2013 |
| WO | 2015/072069 A1 | 5/2015 |

* cited by examiner

- DIRECTION OF FACE (YAW/ PITCH/ ROLL)
- POSITION OF FACE (HORIZONTAL/ VERTICAL/ DEEP)

FIG. 5

DRIVER MONITORING APPARATUS

CROSS REFERENCE TO RELATED APPLICATION

The present disclosure is based on Japanese Patent Application No. 2013-235105 filed on Nov. 13, 2013, the disclosure of which is incorporated herein by reference.

TECHNICAL FIELD

The present disclosure relates to a driver monitoring apparatus that monitors a driver of a vehicle.

BACKGROUND ART

Such a driver monitoring apparatus is publicly known which makes a request to a driver for a special action to keep wakefulness of the driver when a wakefulness level of the driver is low (see, e.g., Patent Literature 1).

PRIOR ART LITERATURES

Patent Literature

Patent Literature 1: JP 2010-020618 A

SUMMARY OF INVENTION

The driver monitoring apparatus is required to keep the wakefulness of the driver even when failing to recognize the wakefulness correctly.

It is an object of the present disclosure to provide a driver monitoring apparatus, which monitors a driver of a vehicle, keeps wakefulness of the driver even when failing to recognize the wakefulness.

To achieve the object, according to an example of the present disclosure, a driver monitoring apparatus is provided to include a control circuit controlling a driver monitoring. The control circuit includes a state recognition section, a recognition stability determination section, an action request section, and an action detection section. The state recognition section recognizes a state of the driver. The recognition stability determination section determines a recognition stability recognized by the state recognition section. When the recognition stability is less than a predetermined reference value, the action request section makes a request to the driver for either (i) a different action that is different from an action requested when the recognition stability is not less than the reference value, or (ii) the action at a different timing, the different timing being different from a timing at which the action is requested when the recognition stability is not less than the reference value. The action detection section detects an action of the driver that responds to the request.

Such a driver monitoring apparatus requires some sort of action of a driver when the recognition stability is less than a reference value; thus, even when the driver state such as wakefulness of the driver cannot be correctly recognized, the wakefulness of the driver can be kept.

A different action that is different from an action requested when the recognition stability is not less than the reference value includes any action not required when the recognition stability is not less than the reference value. That is, an action requested when the recognition stability is less than the reference value only needs to be other than an action requested when the recognition stability is not less than the reference value.

Further, to achieve the object, a driver monitoring program product may be provided which serves as a method including an instruction executed by a computer to realize the sections in the driver monitoring apparatus, the product being stored in a non-transitory computer-readable storage medium.

BRIEF DESCRIPTION OF DRAWINGS

The above and other objects, features and advantages of the present disclosure will become more apparent from the following detailed description made with reference to the accompanying drawings. In the drawings.

DESCRIPTION OF EMBODIMENTS

Hereinafter, an embodiment according to the present disclosure will be described with reference to the drawings.

[Configuration of the Present Embodiment]

A driver monitoring system 1 according to an embodiment of the present disclosure is mounted in a vehicle such as a passenger car, monitoring the wakefulness of a driver of the vehicle when an autopilot system 25 controls the driving of the vehicle automatically or semi-automatically. This driver monitoring system 1 has a function of (i) calling the attention of the driver when recognizing a state where the level of the wakefulness of the driver is low (state where the driver feels sleepy); and (ii) requesting the driver to take some sort of action when failing to recognize the wakefulness of the driver clearly. The vehicle mounted with the driver monitoring system 1 is also referred to as a host vehicle or subject vehicle.

Figure 1:
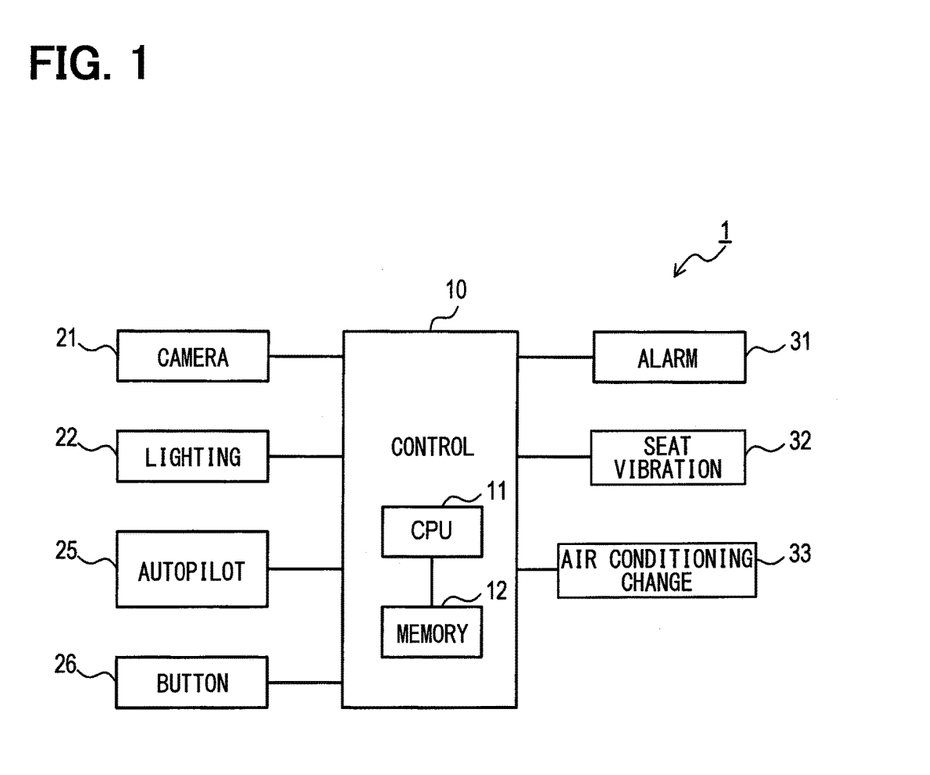
FIG. 1 is a block diagram illustrating a general configuration of a driver monitoring system according to an embodiment of the present disclosure.

In detail, the driver monitoring system 1, as in FIG. 1, includes a control circuit 10, a camera 21, a lighting unit 22, an autopilot system 25, a push button 26, an alarm unit 31, a seat vibration unit 32, and an air-conditioning change unit 33.

The camera 21 is arranged in front of the driver in the vehicle to cover the face of the driver within an imaging range.

The lighting unit 22, which functions as an auxiliary light source for the camera 21, applies an infrared light to the face of the driver. The timing of applying the infrared light may be set to permit either the infrared light to be always applied, or the control circuit 10 to control a light emission timing so as to be synchronous with an imaging period by the camera 21.

The autopilot system 25 accelerates or decelerates and steers the vehicle to thereby control (automatically drive) the vehicle without driver's manipulation. The autopilot system 25 transmits a signal indicating whether the vehicle is automatically driven to the control circuit 10. The autopilot system 25 may be set to perform a semi-automatic driving that controls either (i) the steering of the vehicle or (ii) the acceleration or deceleration of the vehicle.

The push button 26 is constructed as a physical switch arranged within a range that the driver can reach. Manipulating the push button 26 is designed to be recognized by the control circuit 10.

The alarm unit 31, which is used to call the attention of the driver by sound or light, operates when receiving a command from the control circuit 10.

The seat vibration unit 32, which serves as a vibrator embedded in a driver's seat, operates when receiving a command from the control circuit 10.

The air-conditioning change unit 33 has a function of changing the volume, direction, or temperature of air of an air conditioner in the vehicle upon receiving a command from the control circuit 10.

The control circuit 10 may also be provided as a part of a driver monitoring apparatus included in the driver monitoring system. The control circuit 10 is constructed as a well-known computer including a CPU 11 and a memory such as a ROM and a RAM. The CPU 11 performs various processing or processing of a flowchart, which will be described later, according to a program stored in a memory 12.

It is noted that a flowchart or the processing of the flowchart in the present application includes sections (also referred to as steps), each of which is represented, for instance, as S10. Further, each section can be divided into several sub-sections while several sections can be combined into a single section. Furthermore, each of thus configured sections can be also referred to as a device, module, or means. Each or any combination of sections explained in the above can be achieved as (i) a software section in combination with a hardware unit (e.g., computer) or (ii) a hardware section, including or not including a function of a related apparatus; furthermore, the hardware section (e.g., integrated circuit, hard-wired logic circuit) may be constructed inside of a microcomputer.

[Processing of the Present Embodiment]

Figure 2:
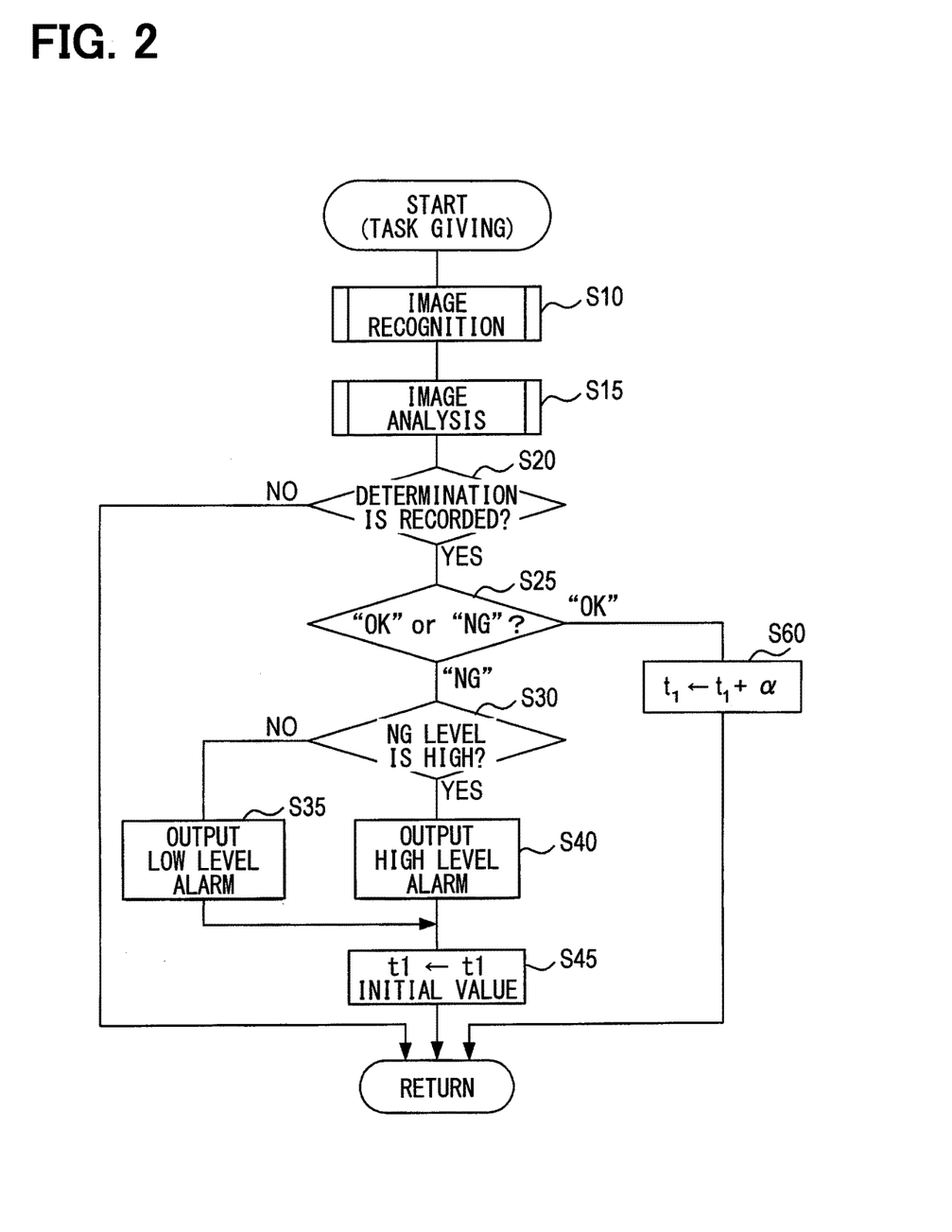
FIG. 2 is a flowchart illustrating task giving processing performed by a control circuit.

In the driver monitoring system 1, the control circuit 10 performs task giving processing shown in FIG. 2. The task giving processing gives the driver a task (instruction) to make some sort of action so as to make sure that the driver does not sleep. However, in the present embodiment, to reduce a burden to the driver, the task giving process is set as not giving the driver any task when the wakefulness of the driver is clear, while as giving the driver a task to check the wakefulness of the driver when the wakefulness of the driver is not clear.

The task giving processing is started when the power of the autopilot system 25 is turned on.

Figure 3:
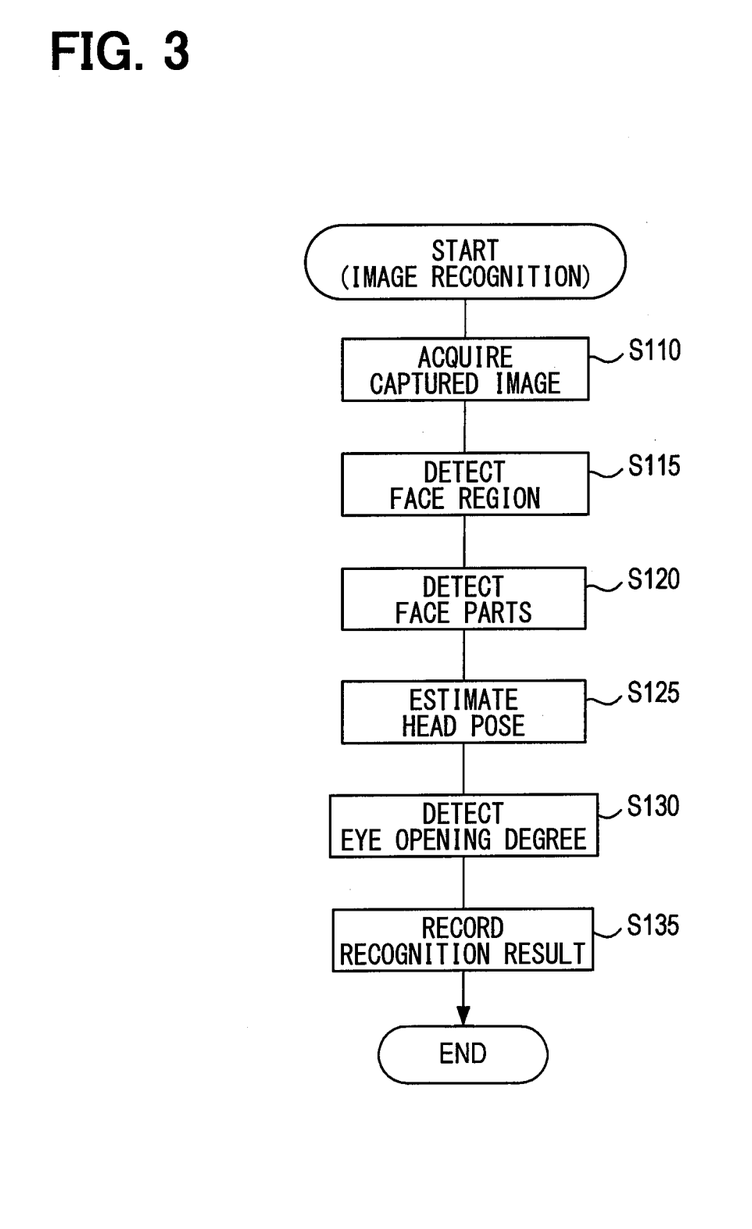
FIG. 3 is a flowchart illustrating image recognition processing.

In more detail, as in FIG. 2, image recognition processing for recognizing the driver state from a captured image by the camera 21 is first performed (S10) to acquire a captured image by the camera 21 (S110) in FIG. 3.

Subsequently, a face region is extracted from the captured image (S115); face parts are extracted (S120). Such processing, as in FIG. 4 (a), subjects the captured image to image processing, recognizing (i) a region which is likely to be the shape of a face and then (ii) a rectangular region including the region as the face region. Then, edges (parts exhibiting a difference not less than a reference value in brightness between pixels arranged next to each other) are detected in the face region; their shapes are recognized, thereby identifying the face parts.

Subsequently, a head pose is estimated (S125). This processing estimates the direction of the face based on the position relationship of the face parts, as in FIG. 4 (b).

Figure 4:
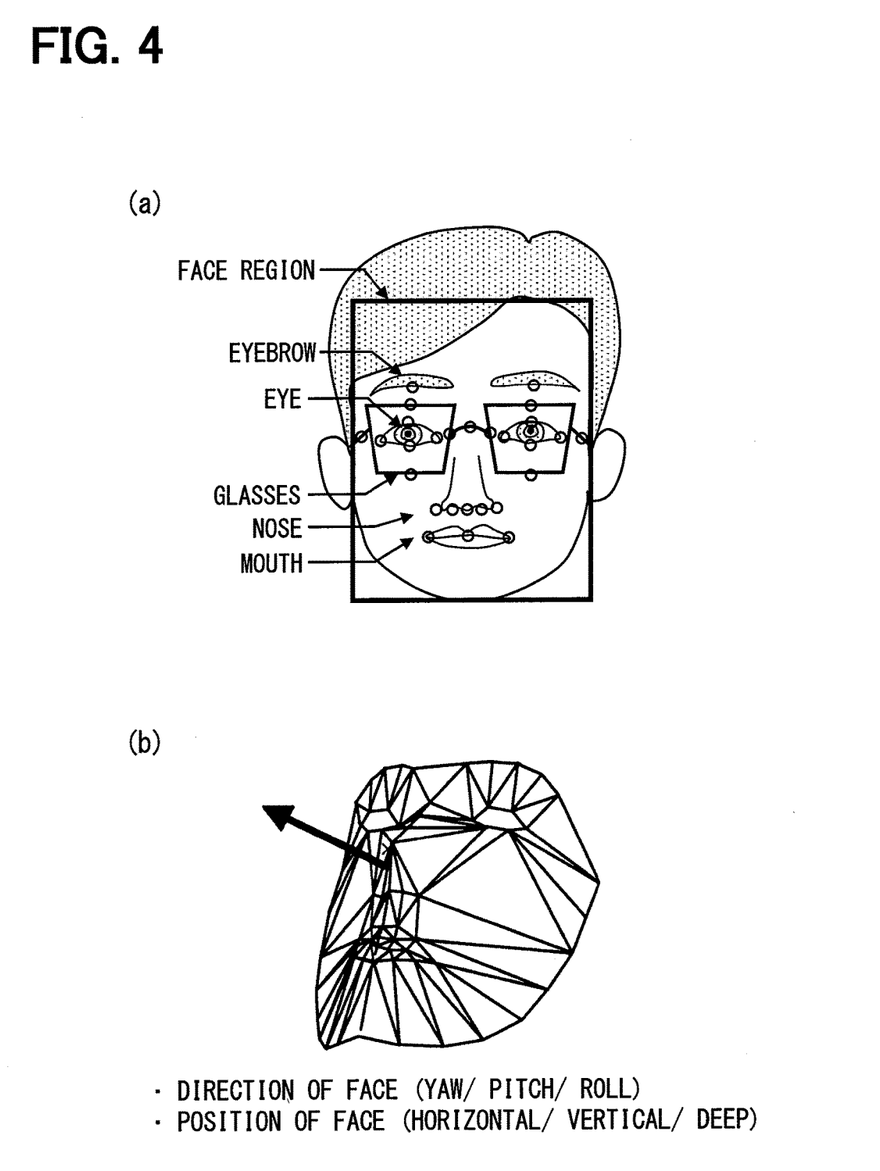
FIG. 4 is a diagram illustrating an specific example recognizing a face part and the direction of a face.

Next, an eye opening degree is estimated (S130). The processing pays attention to a part of an eye of the face parts and finds, e.g., a radius of curvature of a curve of an eyelid (upper edge of an eyeball). The eye opening degree is determined to be lower as the radius of curvature is larger.

Subsequently, an estimation result of the eye opening degree is recorded (S135). However, when the face parts cannot be extracted or the eye opening degree cannot be estimated, that effect is recorded in the memory.

When such processing is finished, the image recognition processing is finished. The routine then returns to FIG. 2, to perform image analysis processing (S15). The image analysis processing recognizes the state of an image by using a recognition result by the image recognition processing and requires the driver to take an action if necessary. Further, the image analysis processing calls the attention of the driver if necessary.

Figure 5:
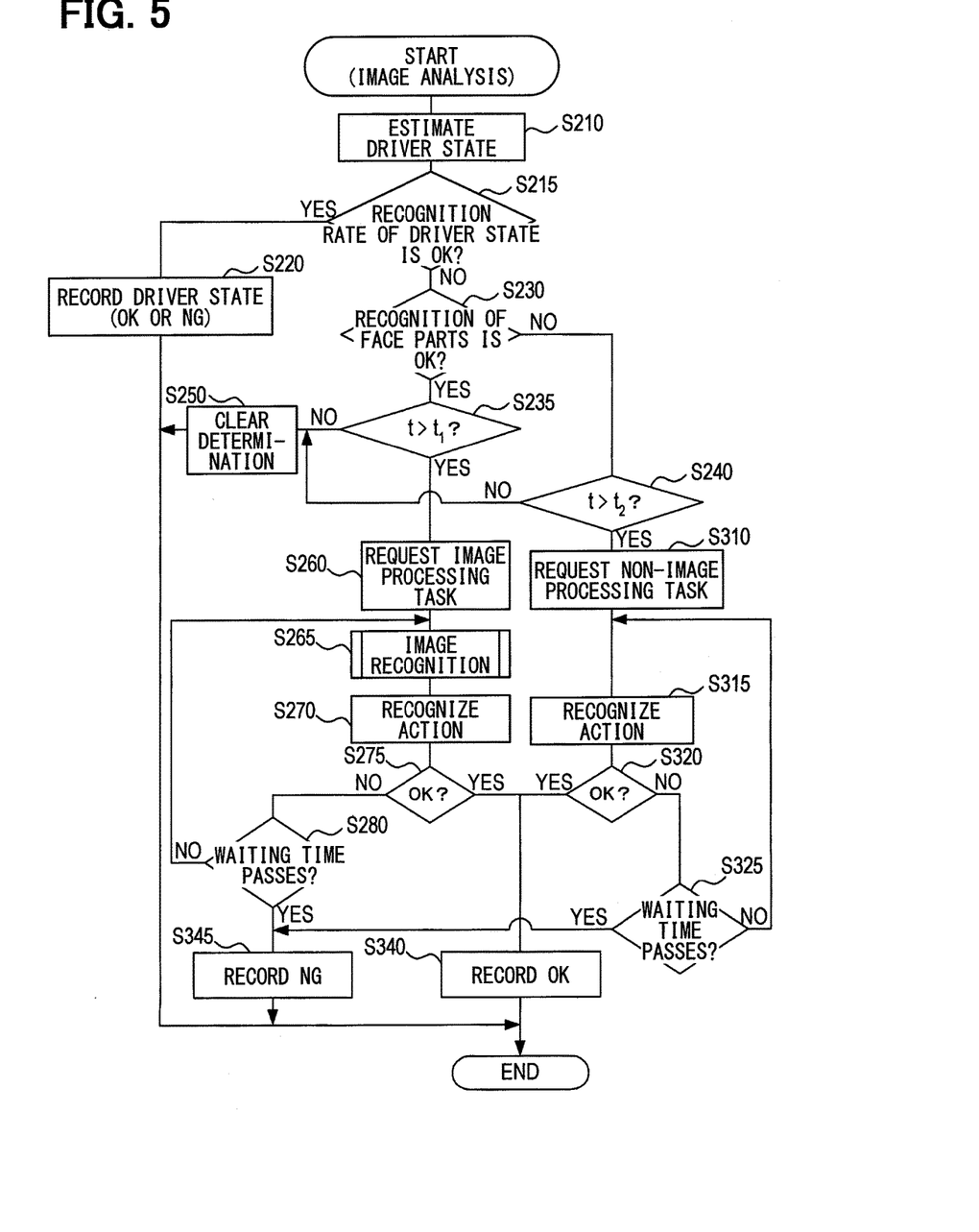
FIG. 5 is a flowchart illustrating image analysis processing.

As in FIG. 5, the image analysis processing first estimates a driver state (S210), which signifies the wakefulness of the driver. However, the wakefulness is only one of the driver states, which may include the state of health of the driver such as the occurrence of a heart attack and the state of driver looking aside during driving while manipulating a mobile phone or a car navigation unit.

To estimate the wakefulness of the driver in the present embodiment, first, for example, an average eye opening degree and the number of blinks of past five seconds are found from an eye opening degree recorded in the memory 12. Then, if the average eye opening degree and the number of blinks are less than respective predetermined threshold values, it is determined that a wakefulness level is low (the driver feels sleepy). In contrast, if the average eye opening degree and the number of blinks are not less than the respective threshold values, it is determined that the wakefulness level is high (the driver does not feel sleepy).

Subsequently, the recognition rate of the driver state is compared with a predetermined determination recognition rate (S215), which is a reference to determine whether or not the state of the driver is reliable and is set at a value of 70 to 90%, for example.

The recognition rate of the wakefulness of the driver indicates a rate at which the recognition result of the eye opening degree is recorded in the memory 12. More specifically, the recognition rate of the wakefulness of the driver indicates a rate of the number of frames in which the average eye opening degree can be normally recognized to the number of captured images (number of frames) acquired for past five seconds, for example.

In the present embodiment, when the driver state is recognized, a recognition result is recorded in the memory 12, but a recognition state flag (likelihood of certainty of recognition) may be outputted.

If the recognition rate of the driver state is not less than a determination threshold value (S215: YES), an estimation result of the driver state is recorded in the memory 12 (S220). When the wakefulness level is high, an estimation result to the effect that the driver state is OK is recorded, whereas when the wakefulness level is low, an estimation result to the effect that the driver state is NG (NO GOOD) is recorded. When the processing of S220 is finished, the image analysis processing is finished.

If the recognition rate of the driver state is less than the determination threshold value (S215: NO), it is determined whether the face parts are recognized in the newest captured image (S230). When the face parts are recognized (S230: YES), a driving duration time t is compared with an image task requiring time t1 (S235).

The driving duration time t indicates a time that passes from when the driver state is last recognized or from when the action responsive to the request made to the driver is last recognized. That is, the driving duration time t is reset when the driver state is recognized (the processing of S220 is performed) or when the action responsive to the request made to the driver is recognized (the processing of S340 is performed).

The image task requiring time t1 indicates a period at which a driver action, which can be recognized by the image processing is requested. Such period is a predetermined value, which can be changed by processing described later.

If the driving duration time t is not more than the image task requiring time t1 (S235: NO), the processing clears the determination result recorded in the memory 28 (S250) and the image analysis processing is finished. The memory 28 records the determination result of the state of the driver or the determination result of the action responsive to the request, which is described later.

If the driving duration time t is more than the image task requiring time t1 (S235: YES), image processing task is required (S260). The image processing task is to request the driver to open his mouth, change the direction of their face, or wink, thereby allowing the image processing to detect the action of the driver. In more detail, the image processing task makes a request to the driver for changing the position relationship of the face parts to the camera 21 in the captured image.

Subsequently, the image recognition processing is again performed (S265) and then an action responsive to the request is recognized (S270). That is, recognizing a change in the position relationship of the face parts before and after the request leads to recognizing that the driver responds to the request.

Then, it is determined whether the action responsive to the request is recognized (S275). When the action responsive to the request is recognized (S275: YES), the effect that the action responsive to the request is recognized (OK) is recorded in the memory 12 (S340).

When the action responsive to the request is not recognized (S275: NO), it is determined whether a waiting time passes, the waiting time which is acquired by adding an allowance time to a time lag (delay time) from when the request is made to when the driver makes an action (S280). When the waiting time does not pass (S280: NO), the routine returns to the processing of S265.

When the waiting time passes (S280: YES), the effect that the action responsive to the request is not recognized (NG) is recorded in the memory 12 (S345). When this processing is finished, the image analysis processing is finished.

If it is determined at S230 that the face parts are not recognized (S230: NO), the driving duration time t is compared with a non-image task requiring time t2 (S240). The non-image task requiring time t2 indicates a period at which the action of the driver recognized without the image processing is requested, and is set at a value not more than the image task requiring time t1.

If the driving duration time t is not more than the non-image task requiring time t2 (S240: NO), the routine proceeds to the processing of S250. Further, if the driving duration time t is more than the non-image task requiring time t2 (S240: YES), a non-image task is required (S310).

The non-image task requests an action for detecting the action of the driver without the image processing and makes a request of pushing the push button 26 in the present embodiment. Subsequently, an action responsive to the request is recognized (S315). This processing detects a signal from the push button 26.

Subsequently, it is determined whether the action responsive to the request is recognized (S320). When the action responsive to the request is recognized (S320: YES), the routine proceeds to the processing of S340. Further, when the action responsive to the request is not recognized (S320: NO), it is determined whether the waiting time passes from when the request is made (S325). When the waiting time does not pass from when the request is made (S325: NO), the routine returns to the processing of S315.

When the waiting time passes from when the request is made (S325: YES), the routine returns to the processing of S345.

When such image analysis processing is finished, the routine returns to FIG. 2. It is determined whether or not the determination result of either OK or NG is recorded in the memory 12 (S20). This determination is negated when the determination result is cleared at S250, and is affirmed in the other case.

If the determination result is not recorded (S20: NO), the routine returns to the processing of S10. If the determination result is recorded (S20: YES), it is determined whether the determination result is OK or NG.

When the determination result is OK (S25: OK), the image task requiring time t1 is increased by a (a is, e.g., as large a value as 1 minute) (S60) and then the routine returns to S10. When the determination result is NG (S25: NG), an NG level is determined (S30).

This NG level is assigned with a specified value according to a frequency at which NG is determined or a kind of processing when NG is determined, the kind includes NG being determined by the eye opening degree, or failing to detect any action responding to the request. The NG level assigned with the value more than a threshold value of a reference is determined to be high.

If the NG level is low (S30: NO), an alarm of a low level is outputted (S35). The alarm of the low level indicates, e.g., an alarm by the alarm unit 31.

If the NG level is high (S30: YES), an alarm of a high level is outputted (S40). The alarm of the high level indicates, e.g., not only the alarm by the alarm unit 31 but also processing for giving the driver the seat vibration by the seat vibration unit 32 and processing for applying cool air to the face of the driver by the air-conditioning change unit 33. That is, the alarm of the high level gives the driver an alarm stronger than the alarm of the low level to thereby strongly call the attention of the driver.

When the processing of calling the attention of the driver is finished in S35 or S40, the image task requiring time t1 is returned to an initial value (S45) and then the routine returns to the processing of S10.

[Effect of the Present Embodiment]

In the above driver monitoring system 1, the control circuit 10 recognizes the driver state and determines a recognition stability. When the recognition stability is less than a predetermined reference value, the driver is requested to make an action different from an action requested when the recognition stability is not less than the reference value, or even when the same action is requested, the driver is requested to make the action at a different timing. Then, the action of the driver to the request is detected.

Such a configuration can keep the wakefulness of the driver even when the driver state such as wakefulness cannot be correctly recognized, since the driver is requested to make some sort of action when the recognition stability is less than the reference value.

Recognizing stably the face parts at any time is not easy for the image processing. The disturbance light (direct sunlight or unbalanced irradiation of the sunlight to the driver's face) or the reflection of a scene in the glasses may bring the recognition continuously or intermittently into an erroneous detection or a not-yet detection. In such case, the present embodiment secures the stability by performing the non-image processing task even while giving trouble to the driver.

The control circuit 10 in the driver monitoring system 1 acquires the captured image of the driver's face and recognizes the constituent elements of the driver's face from the captured image. Then, when the recognition stability is less than the predetermined reference value and, simultaneously, a predetermined part of the constituent elements of the driver's face cannot be recognized, the control circuit 10 requires a non-imaging action for detecting the action of the driver without the image processing.

Such a driver monitoring system 1 requires a driver's action (non-imaging action) that can be detected without using the image processing, thereby reliably detecting the driver's action.

Further, when, of the constituent elements of the driver's face, a predetermined part (face part) is recognized, the control circuit 10 in the driver monitoring system 1 requires an action of the driver at intervals of the reference period (t1). In contrast, when the predetermined part is not recognized, the control circuit 10 requires the action of the driver at intervals of a shorter period (t2) than the reference period (t1).

The predetermined part signifies face parts required at least for estimating the direction of the face, e.g., a combination of the nose and the width of the face, or a combination of the nose and both the eyes. Further, the predetermined part for estimating sleepiness may be the eye opening degree of at least either the left eye or the right eye.

Such a driver monitoring system 1 can easily keep the wakefulness of the driver, since the period at which the action is required of the driver is shortened when the predetermined part cannot be recognized.

When the predetermined part can be recognized, the control circuit 10 in the driver monitoring system 1 requires an action to change the predetermined part, whereas when the predetermined part cannot be recognized, the control circuit 10 requires an action that can be detected by a detector (push button 26) for detecting the operation of the driver.

Such a driver monitoring system 1 can reduce the burden of the driver, since the action that can be recognized by the image is required of the driver when the predetermined part can be recognized. In contrast, when the predetermined part cannot be recognized, the action that can be detected by the detector is required of the driver. Hence, the action by the driver can be reliably detected.

Further, in the driver monitoring system 1, when the action of the driver responsive to the request cannot be detected or the recognized driver state is likely to pose a difficulty for the driving, the control circuit 10 calls the attention of the driver.

Such a driver monitoring system 1 can call the attention of the driver so as not to pose a difficulty for the driving. Further, when the action of the driver responsive to the request is detected or the driver state does not pose a difficulty for the driving, calling the attention of the driver is prevented. This reduces unnecessary warning against the driver.

Further, in the driver monitoring system 1, the control circuit 10 prohibits calling any attention of the driver within a predetermined attention calling interval time after having called the driver's attention. However, the present embodiment calls the driver's attention when recognizing that "the driver state is likely to pose a difficulty for the driving."

Such a driver monitoring system 1 can reduce an annoyance due to calling the attention frequently.

Further, in the driver monitoring system 1, the control circuit 10 changes the attention calling interval time to be longer when having detected the action of the driver, and to be shorter when having called the attention.

Such a driver monitoring system 1 can prevent the driver from feeling annoyed and keep the wakefulness of the driver at the same time, by changing the attention calling interval time.

Also when the driver state can be recognized by image recognition processing, the attention calling interval time may be changed to be longer.

Other Embodiments

It should not be understood that the present disclosure is limited to the above embodiment. The present disclosure may also be provided as the following configuration which includes a part(s) different from the above embodiment. The configuration other than the different part is the same as that in the above embodiment, so that the drawings in the above embodiment can also be referred to.

For example, in the embodiment, the configuration for detecting the manipulation of the driver without using the image processing is requiring a driver to push the push button 26 and detecting the manipulation to the button 26. Instead of pushing the push button 26, manipulating a pedal or steering wheel may be required, and detected with a sensor installed in the pedal or steering wheel.

Further, the embodiment employs the configuration not requiring any action when the driver state is clear. However, even when the driver state is clear, some sort of action may be required with given time intervals. This case may employ a configuration lengthening a period at which the action is required than a period set when the driver state is not clear, or a configuration requiring a lighter action not to impose a burden on the driver.

That is, the action required even when the driver state is clear only need be different from the action required when the driver state is not clear.

The following points will be noted. The push button 26 in the embodiment is also referred to as a detector or a detection device or means. Further, of the processing performed by the control circuit 10 in the embodiment, the processing of S30, S35, and S40 is also referred to as an attention calling section, device, or means, and the processing of S45 and S60 is also referred to as an interval time changing section, device, or means.

Further, in the embodiment, of the processing performed by the control circuit 10, the processing of S110 is also referred to as a captured image acquisition section, device, or means, and the processing of S120 is also referred to as a face recognition section, device, or means. Still further, the processing of S210 is also referred to as a state recognition section, device, or means, and the processing of S215 is also referred to as a recognition stability determination section, device, or means.

Still further, in the embodiment, of the processing performed by the control circuit 10, the processing of S230, S235, S240, S260, and S310 is also referred to as an action request section, device, or means, and the processing of S235, S240, and S250 is also referred to as an attention prohibition section, device, or means. Still further, the processing of S270 and S315 is also referred to as an action detection section, device, or means.

While the present disclosure has been described with reference to embodiments thereof, it is to be understood that the disclosure is not limited to the embodiments and configurations. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. A driver monitoring apparatus that monitors a driver of a vehicle, the driver monitoring apparatus including a control circuit that controls monitoring of the driver,
the control circuit comprising:
a state recognition device that recognizes a state of the driver;
a recognition stability determination device that determines a recognition stability of a recognized state output by the state recognition device;
an action request device that makes a request to the driver, the action request device making the request to the driver to perform a first action at a first timing when the recognition stability is not less than a reference value,
wherein, when the recognition stability is less than the predetermined reference value, the action request device makes the request to the driver to perform either
a second action that is different from the first action requested when the recognition stability is not less than the reference value, or
the first action at a second timing that is different from the first timing at which the first action is requested when the recognition stability is not less than the reference value; and
an action detection device that detects an action performed by the driver that responds to the request.

2. The driver monitoring apparatus according to claim 1, wherein:
the control circuit further includes
a captured image acquisition device that acquires a captured image of a face of the driver, and
a face recognition device that recognizes a component of the face of the driver from the captured image; and
when the recognition stability is less than the reference value and, simultaneously, a predetermined part that is within the component of the face of the driver is not recognized,
the action request device makes the request to the driver to perform a non-image action enabling the action detection device to detect an action of the driver without using image processing.

3. The driver monitoring apparatus according to claim 2, wherein:
when the predetermined part is recognized, the action request device makes the request to the driver to perform an action at intervals of a reference period; and
when the predetermined part is not recognized, the action request device makes the request to the driver to perform an action at intervals of a period shorter than the reference period.

4. The driver monitoring apparatus according to claim 2, wherein:
when the predetermined part is recognized, the action request device makes the request to the driver to perform an action to change the predetermined part; and
when the predetermined part is not recognized, the action request device makes the request to the driver to perform an action that is detected by a detector that detects the driver performing the action.

5. The driver monitoring apparatus according to claim 1, wherein,
the control circuit further includes an attention calling device that calls an attention of the driver either
when the action detection device fails to detect an action of the driver responding to the request, or
when a state of the driver recognized by the state recognition device that is likely to pose a difficulty for driving.

6. The driver monitoring apparatus according to claim 5, wherein
the control circuit further includes an attention prohibition device that prohibits the attention calling device from calling an attention within a predetermined attention calling interval time after having called the attention.

7. The driver monitoring apparatus according to claim 6, wherein:
the control circuit further includes an interval time changing device that
shortens the attention calling interval time when the action detection device detects an action of the driver, and
lengthens the attention calling interval time when the attention calling device calls the attention of the driver.

* * * * *